(12) United States Patent
Fang et al.

(10) Patent No.: US 12,398,353 B2
(45) Date of Patent: Aug. 26, 2025

(54) FULL-OCEAN-DEPTH FIDELITY ENZYMOLOGICAL MEASUREMENT DEVICE FOR MICROBIAL EXTRACELLULAR ENZYMES

(71) Applicant: Shanghai Ocean University, Shanghai (CN)

(72) Inventors: Jiasong Fang, Shanghai (CN); Junwei Cao, Shanghai (CN); Jiawang Chen, Shanghai (CN); Binbin Pan, Shanghai (CN); Hongge Zhang, Shanghai (CN); Han Ge, Shanghai (CN); Dahai Zhang, Shanghai (CN); Yuan Lin, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 762 days.

(21) Appl. No.: 17/735,364

(22) Filed: May 3, 2022

(65) Prior Publication Data
US 2022/0356426 A1 Nov. 10, 2022

(30) Foreign Application Priority Data

May 4, 2021 (CN) .......................... 202110487170.7
Jun. 18, 2021 (CN) .......................... 202110680479.8

(51) Int. Cl.
*C12M 1/00* (2006.01)
*C12M 1/12* (2006.01)
(Continued)

(52) U.S. Cl.
CPC ............ *C12M 21/18* (2013.01); *C12M 23/08* (2013.01); *C12M 23/38* (2013.01); *C12M 33/04* (2013.01);
(Continued)

(58) Field of Classification Search
CPC .......................... G01N 2001/1427; G01N 1/12
See application file for complete search history.

(56) References Cited

U.S. PATENT DOCUMENTS 3,892,130 A * 7/1975 Winget .................... G01N 1/12
73/863.42
12,235,195 B1 * 2/2025 Duan ........................ G01N 1/10
(Continued)

OTHER PUBLICATIONS

Das et al. (2015) Data-driven robotic sampling for marine ecosystem monitoring. International Journal of Robotic Research, 34(12), 1435-1452.*

*Primary Examiner* — Nathan A Bowers
(74) *Attorney, Agent, or Firm* — Day Pitney LLP; George Chaclas; Anthony A. Kassas

(57) ABSTRACT

A full-ocean-depth fidelity enzymological measurement device for microbial extracellular enzyme is provided, comprising a pressure-maintaining sampling bottle, pressure-maintaining transfer equipment, a pressure-maintaining enzymological reactor, and heat preservation equipment and enzyme activity detection equipment. The pressure-maintaining enzymological reactor comprises a barrel body, a plug, polytetrafluoroethylene gaskets, an O-ring, a piston, a high-pressure straight-through valve, and a high-pressure connector. The pressure-maintaining enzymological reactor is in a closed barrel body shape and is internally provided with the piston, and the plug and the valve are arranged at each of two ends of the pressure-maintaining enzymological reactor; and the valve is connected to the pressure-maintaining transfer equipment through the high-pressure connector. According to the full-ocean-depth fidelity enzymological measurement device provided by the present disclosure, full-ocean-depth (0-11000 m) sample pressure-maintaining sampling and transferring can be achieved; and sample collection, transferring and enzymological reaction
(Continued)

can be conducted under in-situ pressure and temperature conditions.

9 Claims, 2 Drawing Sheets

(51) Int. Cl.
 *C12M 1/24* (2006.01)
 *C12M 1/26* (2006.01)
 *C12M 1/34* (2006.01)
 *C12M 1/40* (2006.01)
 *G01N 1/00* (2006.01)

(52) U.S. Cl.
 CPC ............ *C12M 37/04* (2013.01); *C12M 41/40* (2013.01); *C12M 41/46* (2013.01)

(56) References Cited

U.S. PATENT DOCUMENTS

| | | | |
|---|---|---|---|
| 12,247,991 B2* | 3/2025 | Pracheil | G01N 1/10 |
| 2013/0269423 A1* | 10/2013 | Angelescu | G01N 11/02 |
| | | | 73/54.01 |
| 2015/0224502 A1* | 8/2015 | Pargett | G01N 33/1893 |
| | | | 422/509 |
| 2019/0368978 A1* | 12/2019 | Sheryll | E21B 7/124 |
| 2022/0033872 A1* | 2/2022 | Magalhães | G01N 1/12 |

* cited by examiner

FULL-OCEAN-DEPTH FIDELITY ENZYMOLOGICAL MEASUREMENT DEVICE FOR MICROBIAL EXTRACELLULAR ENZYMES

CROSS REFERENCE TO RELATED APPLICATION

This patent application claims the benefit and priority of Chinese Patent Application No. 202110680479.8 filed on Jun. 18, 2021, which claims the benefit and priority of Chinese Patent Application No. 202110487170.7, filed on May 4, 2021, the disclosure of which is incorporated by reference herein in their entirety as part of the present application.

TECHNICAL FIELD

The present disclosure relates to a fidelity enzymological measurement device, and in particular relates to a full-ocean-depth fidelity enzymological measurement device for microbial extracellular enzymes.

BACKGROUND ART

The ocean accounts for more than 70% of the Earth's surface area, and the abyssal region at a depth of 6,000 meters and more accounts for 45% of the vertical depth of the ocean, which has extreme environmental characteristics such as low temperature, high pressure, oligotrophy, and the like. The abyss is the most inaccessible environment on Earth for humans due to the limitations of survey and exploration technologies, which is also a virgin land for resource exploitation and discovery. Due to the extreme environmental characteristics, compared with the well-known terrestrial or shallow sea organisms, the abyssal microbes have special metabolic and physiological adaptation mechanisms and possess special genes, enzymes, and other biological resources. In-depth research and exploitation of the abyssal microbes are gradually becoming a strategic direction and goal for all countries in the world.

How to obtain in-situ fidelity abyssal samples and to study microbial life process under in-situ conditions are critical to help us analyze the structure of microbial communities, enzyme activities, life processes and dynamic response processes of microbes to environmental changes in the marine environment. Wherein the device for accurately measuring the types and activities of the extracellular enzymes of the marine microbes is an essential tool for researching the life process of the marine microbes, and developing and utilizing microbial enzymes and protein resources. In the past, traditional methods usually measure microbial extracellular enzyme activity of the deep ocean under atmospheric temperature and pressure conditions. The obtained data does not represent enzymatic activities under in-situ conditions, and thus seriously limiting our ability to capture, recognize and respond to microbial life processes, enzyme activities and dynamic response processes of microbes to environmental changes in the marine environment. Therefore, it is extremely urgent to invent a fidelity device that is capable of performing full-ocean-depth microbial extracellular enzyme activity measurement.

SUMMARY

An objective of the present disclosure is to provide a fidelity enzymological measurement device for microbial extracellular enzymes, which is capable of being applied to the full ocean depth of 0-11000 meters.

The present disclosure is achieved through the following technical solutions:

a full-ocean-depth fidelity enzymological measurement device for microbial extracellular enzyme is provided, comprising a pressure-maintaining sampling bottle, a pressure-maintaining transfer equipment, a pressure-maintaining enzymological reactor, and a heat preservation and enzyme activity detection equipment, wherein an internal cavity of each of the pressure-maintaining sampling bottle, the pressure-maintaining transfer equipment, the pressure-maintaining enzymological reactor, and the heat preservation and enzyme activity detection equipment is maintained under an in-situ pressure; the pressure-maintaining transfer equipment is configured to transfer a sample under the in-situ pressure; the heat preservation and enzyme activity detection equipment is configured to perform heat insulation, fluorometric measurement and enzyme activity calculation on the sample; the pressure-maintaining enzymological reactor is in a closed barrel body shape, and comprises a barrel body, a plug, a polytetrafluoroethylene gasket, an O-ring, a piston, a high-pressure straight-through valve, a high-pressure connector, first overflow holes for overflow and a second hole for tool operation; the barrel body is a container with openings at two ends, the piston is arranged in the barrel body, and the plug and the valve are arranged at each of the two ends of the barrel body; the valve is connected to the pressure-maintaining transfer equipment through the high-pressure connector, and the plug and the piston are both provided with sealing rings for sealing.

Preferably, the barrel body, the plug and the piston are all made of titanium alloy TC4 which can reduce the influence on the microbes to the greatest extent.

Preferably, the high-pressure straight-through valve is made of stainless steel AISI 304.

Preferably, the O-ring is made of fluorine rubber.

Preferably, the sealing ring is composed of the polytetrafluoroethylene gasket and the O-ring.

Preferably, two opening ends of the barrel body are each provided with internal threads, the plug is provided with external threads, and the barrel body and the plug are connected through the threads.

Preferably, the outside of the plug is provided with external threads, two sides of the high-pressure straight-through valve are each provided with internal threads, and the plug and the high-pressure straight-through valve are connected through the threads.

Preferably, the two opening ends of the barrel body are each provided with the first holes, and each of the first holes is located at an outside position corresponding to the polytetrafluoroethylene gasket and the O-ring on the plug.

Preferably, the outside of the plug is provided with the second hole.

The present disclosure has the beneficial effects that the pressure-maintaining enzymological reactor can be rapidly connected to the pressure-maintaining transfer equipment and the pressure-maintaining sampling bottle through the high-pressure connectors; an enzymological reaction fluorogenic substrate is pre-arranged in the pressure-maintaining enzymological reactor, and then the pressure-maintaining enzymological reactor is placed in a constant-temperature water bath for pressure-maintaining enzymological reaction, that is, sample collection, transferring and enzymological reaction are all conducted under in-situ pressure and temperature conditions. The device has important scientific significance and good application prospect.

Figure 1:
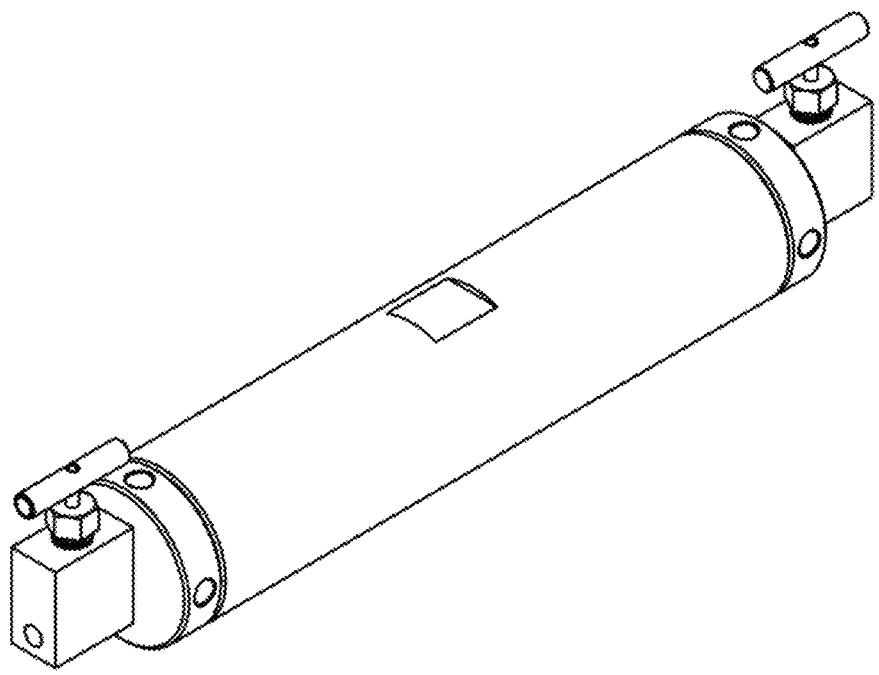
FIG. 1 is a structure diagram of an overall appearance of a pressure-maintaining enzymological reactor.
Figure 2:
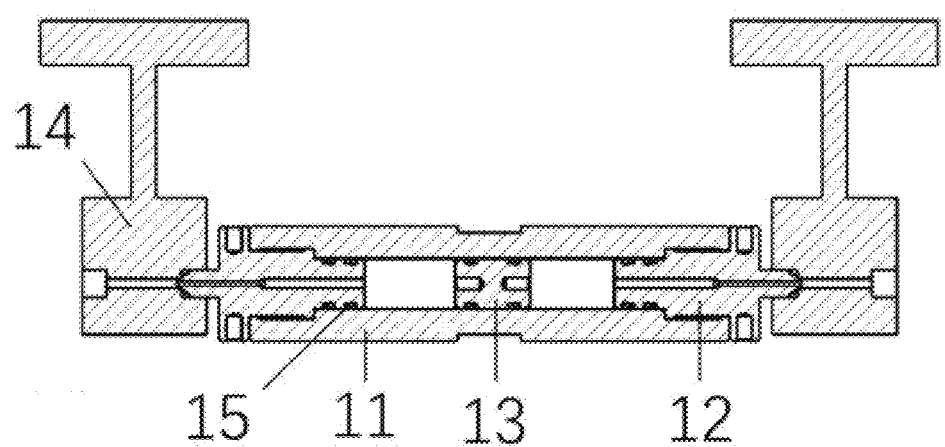
FIG. 2 is a sectional structure diagram of the pressure-maintaining enzymological reactor.

In the drawings:
1—pressure-maintaining enzymological reactor; 2—pressure-maintaining sampling bottle; 3—pressure-maintaining transfer equipment; 4—waste liquid collection device; 5—heat preservation and enzyme activity detection equipment; 11—barrel body; 12—plug; 13—piston; 14—high-pressure straight-valve; 15—sealing ring.

DETAILED DESCRIPTION OF THE EMBODIMENTS

The embodiment of the present disclosure is described in detail below with reference to the accompanying drawings: the embodiment is implemented on the premise of the technical solution of the present disclosure, a detailed implementation mode and a specific operation process are given, but the scope of protection of the present disclosure is not limited to the embodiment described below.

Referring to FIGS. 1-4, a full-ocean-depth fidelity enzymological measurement device for microbial extracellular enzymes provided by the present disclosure comprises a pressure-maintaining sampling bottle 2, a pressure-maintaining transfer equipment 3, a pressure-maintaining enzymological reactor 1, and a heat preservation and enzyme activity detection equipment 5. Wherein the pressure-maintaining enzymological reactor comprises a barrel body 11, two plugs 12, a piston 13, two high-pressure straight-through valves 14, and six pairs of sealing rings 15 composed of polytetrafluoroethylene gaskets and O-rings.

Figure 3:
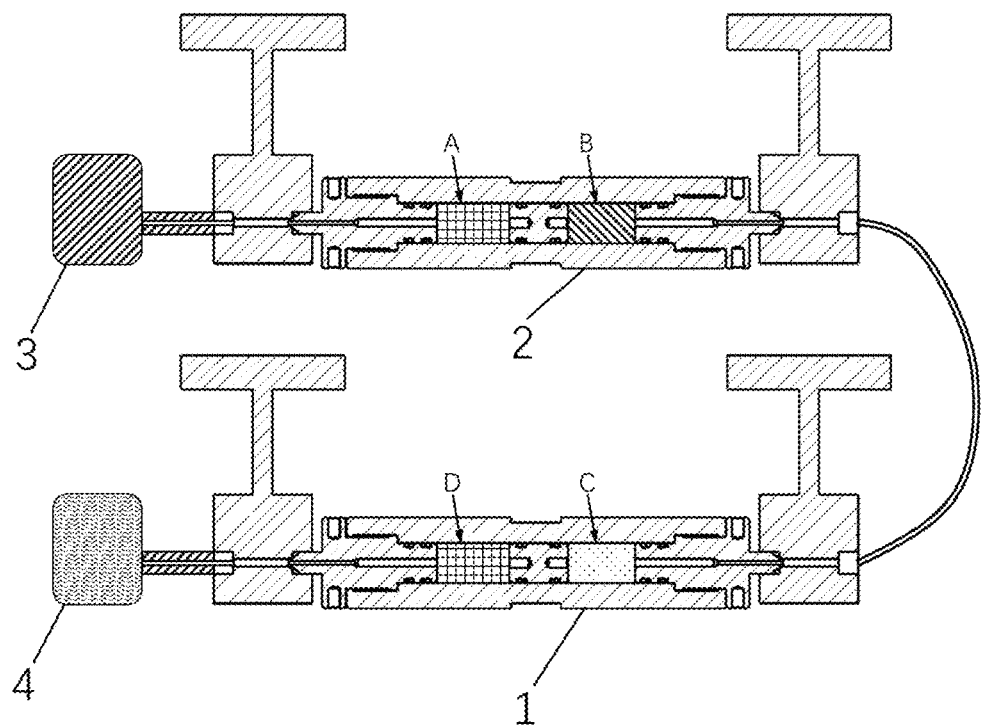
FIG. 3 is a schematic diagram of pressure-maintaining transferring of an in-situ high-pressure sample to a pressure-maintaining reactor.
Figure 4:
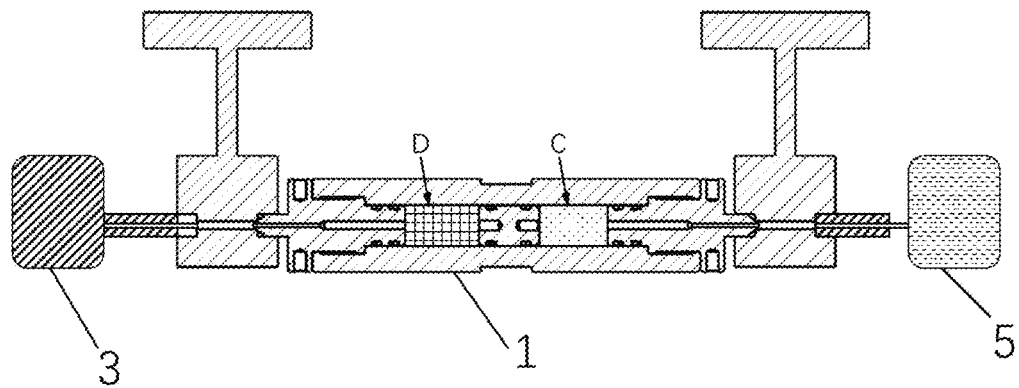
FIG. 4 is a schematic diagram of conducting sampling and measurement on the pressure-maintaining enzymological reactor.

As shown in FIGS. 3-4, during work of the device, firstly, an enzymological reaction fluorogenic substrate is pre-arranged in a chamber C of the pressure-maintaining enzymological reactor 1, and a chamber D of the pressure-maintaining enzymological reactor 1 is filled with sterile tap water (in-situ pressure); ddH$_2$O is injected into a chamber A of the pressure-maintaining sampling bottle through the pressure-maintaining transfer equipment 3 under in-situ pressure, thus a pressure-maintaining seawater sample (a chamber B in FIG. 3) is transferred into the chamber C of the pressure-maintaining enzymological reactor 1 under the in-situ pressure, at the moment, the enzymological reaction fluorogenic substrate is mixed with pressure-maintaining seawater, and an enzymological reaction starts. The high-pressure straight-through valves at two ends are closed, and then the pressure-maintaining enzymological reactor 1 is placed in an in-situ temperature water bath for heat preservation and pressure-maintaining incubation.

When the enzymological reaction reaches the preset time, the sample is transferred by the pressure-maintaining transfer equipment 3 to the heat preservation and enzyme activity detection equipment for fluorometric measurement and enzyme activity calculation. During this process, the sample pressure in the chamber C (FIG. 3) remains unchanged (in situ pressure), and the sample in the heat preservation and enzyme activity detection equipment 5 is subjected to fluorometric measurement under atmospheric pressure conditions for the fluorometric measurement.

The basic principles and principal features of the present disclosure and the advantages of the present disclosure are shown and described above. It should be understood by those skilled in the art that the present disclosure is not limited by the above embodiments, and that above embodiments and the description in the specification are merely illustrative of the principles of the present disclosure, and that various changes and modifications may also be made to the present disclosure without departing from the spirit and scope of the present disclosure, all of which fall within the scope of the present disclosure claimed to be protected. The present disclosure claims a scope of protection defined by the appended claims and equivalents thereof.

What is claimed is:

1. A full-ocean-depth fidelity enzymological measurement device for microbial extracellular enzymes, comprising a pressure-maintaining sampling bottle, a pressure-maintaining transfer equipment, a pressure-maintaining enzymological reactor, and a heat preservation and enzyme activity detection equipment, wherein an internal cavity of each of the pressure-maintaining sampling bottle, the pressure-maintaining transfer equipment, the pressure-maintaining enzymological reactor, and the heat preservation and enzyme activity detection equipment is maintained under an in-situ pressure;

the pressure-maintaining transfer equipment is configured to transfer a sample under the in-situ pressure;

the heat preservation and enzyme activity detection equipment is configured to perform heat insulation, fluorometric measurement and enzyme activity calculation on the sample; and the pressure-maintaining enzymological reactor is in a closed barrel body shape, and comprises a barrel body, a plug, a polytetrafluoroethylene gasket, an O-ring, a piston, a high-pressure straight-through valve, a high-pressure connector, first holes for overflow and a second hole for tool operation; the barrel body is a container with openings at two ends, the piston is arranged in the barrel body, and the plug and the valve are arranged at each of the two ends of the barrel body, the valve is connected to the pressure-maintaining transfer equipment through the high-pressure connector, and the plug and the piston are both provided with sealing rings.

2. The full-ocean-depth fidelity enzymological measurement device for microbial extracellular enzymes according to claim 1, wherein the barrel body, the plug and the piston are all made of titanium alloy TC4.

3. The full-ocean-depth fidelity enzymological measurement device for microbial extracellular enzymes according to claim 1, wherein the high-pressure straight-through valve is made of stainless steel AISI 304.

4. The full-ocean-depth fidelity enzymological measurement device for microbial extracellular enzymes according to claim 1, wherein the O-ring is made of fluorine rubber.

5. The full-ocean-depth fidelity enzymological measurement device for microbial extracellular enzymes according to claim 1, wherein the sealing ring is composed of the polytetrafluoroethylene gasket and the O-ring.

6. The full-ocean-depth fidelity enzymological measurement device for microbial extracellular enzymes according to claim 1, wherein two opening ends of the barrel body are each provided with internal threads, the plug is provided with external threads, and the barrel body and the plug are connected through the threads.

7. The full-ocean-depth fidelity enzymological measurement device for microbial extracellular enzymes according to claim 1, wherein the outside of the plug is provided with external threads, and two sides of the high-pressure straight-through valve are each provided with internal threads, and the plug and the high-pressure straight-through valve are connected through the threads.

8. The full-ocean-depth fidelity enzymological measurement device for microbial extracellular enzymes according to claim 1, wherein the two opening ends of the barrel body are each provided with the first holes, and each of the first holes is located at an outside position corresponding to the polytetrafluoroethylene gasket and the O-ring on the plug.

9. The full-ocean-depth fidelity enzymological measurement device for microbial extracellular enzymes according to claim 1, wherein the outside of the plug is provided with the second hole.

* * * * *